United States Patent [19]

Dobben

[11] Patent Number: 4,994,077
[45] Date of Patent: Feb. 19, 1991

[54] ARTIFICIAL HEART VALVE FOR IMPLANTATION IN A BLOOD VESSEL

[76] Inventor: Richard L. Dobben, 6355 N. 600 West, Michigan City, Ind. 46360

[21] Appl. No.: 342,225

[22] Filed: Apr. 21, 1989

[51] Int. Cl.$^5$ ................................................ A61F 2/24
[52] U.S. Cl. ...................................... 623/2; 606/191; 606/194; 137/521; 137/527
[58] Field of Search .................... 623/2; 128/343, 345; 137/521, 527, 527.8; 606/191, 192, 194

[56] References Cited

U.S. PATENT DOCUMENTS

| | | | |
|---|---|---|---|
| 4,174,913 | 11/1979 | Schliesser | 137/527.8 |
| 4,580,568 | 4/1986 | Gianturco | 128/345 |
| 4,688,553 | 8/1987 | Metals | 128/345 |
| 4,727,873 | 3/1988 | Mobin-Uddin | 128/345 |
| 4,817,600 | 4/1989 | Herms et al. | 128/345 |
| 4,830,003 | 5/1989 | Wolff et al. | 128/343 |

Primary Examiner—Randall L. Green
Assistant Examiner—Stephanie L. Iantorno
Attorney, Agent, or Firm—Laff, Whitesel, Conte & Saret

[57] ABSTRACT

An artificial heart valve is designed to fit into a blood vessel when a patient is too weak to undergo open heart surgery. The valve has a disk shaped flap valve threaded on a bent wire which may be anchored in a blood vessel. One embodiment uses a clip anchor which is bent into somewhat the shape of a safety pin. Another embodiment uses a STENT as the anchor. The wire snags on the wall of the blood vessel in order to keep the valve from migrating through the blood vessel. The flap valve opens and closes under the pressure of blood which is ebbing and flowing responsive to a pumping heart.

27 Claims, 2 Drawing Sheets

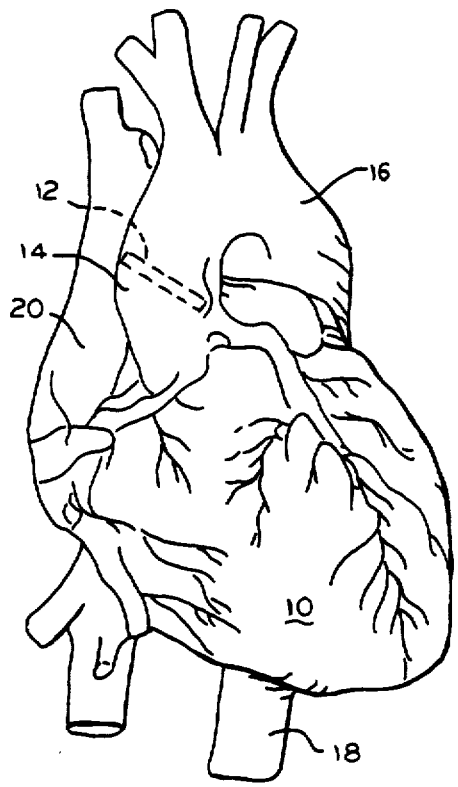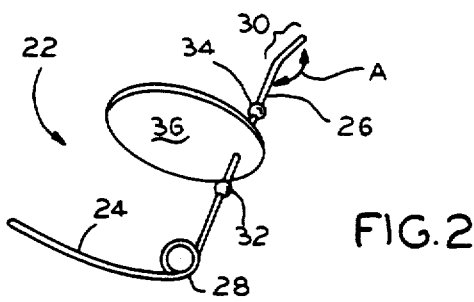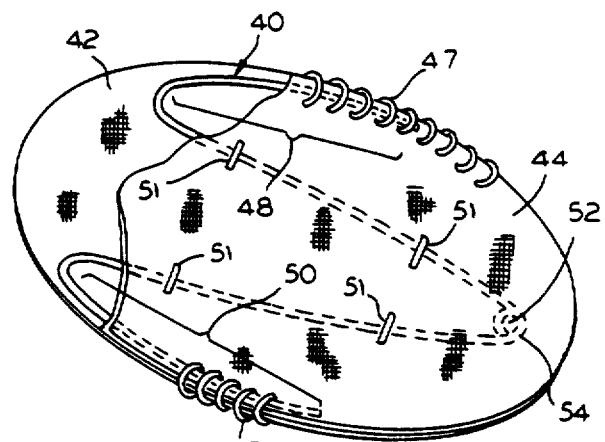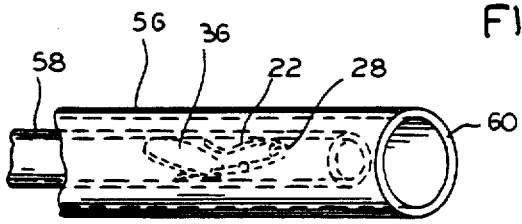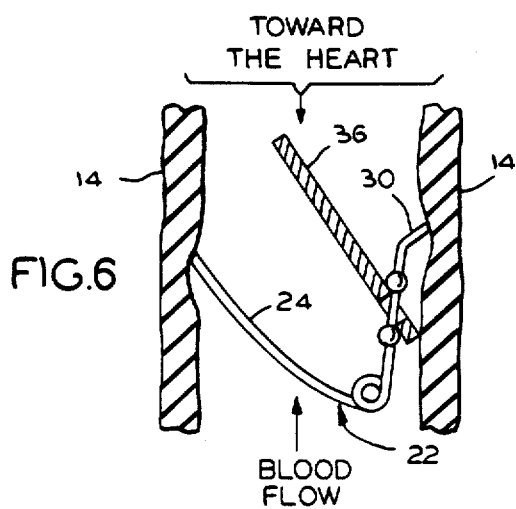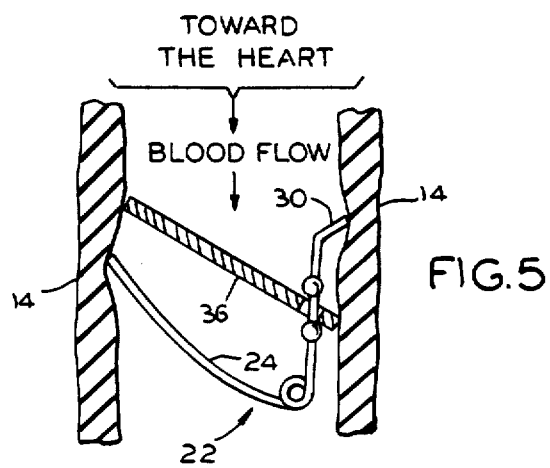

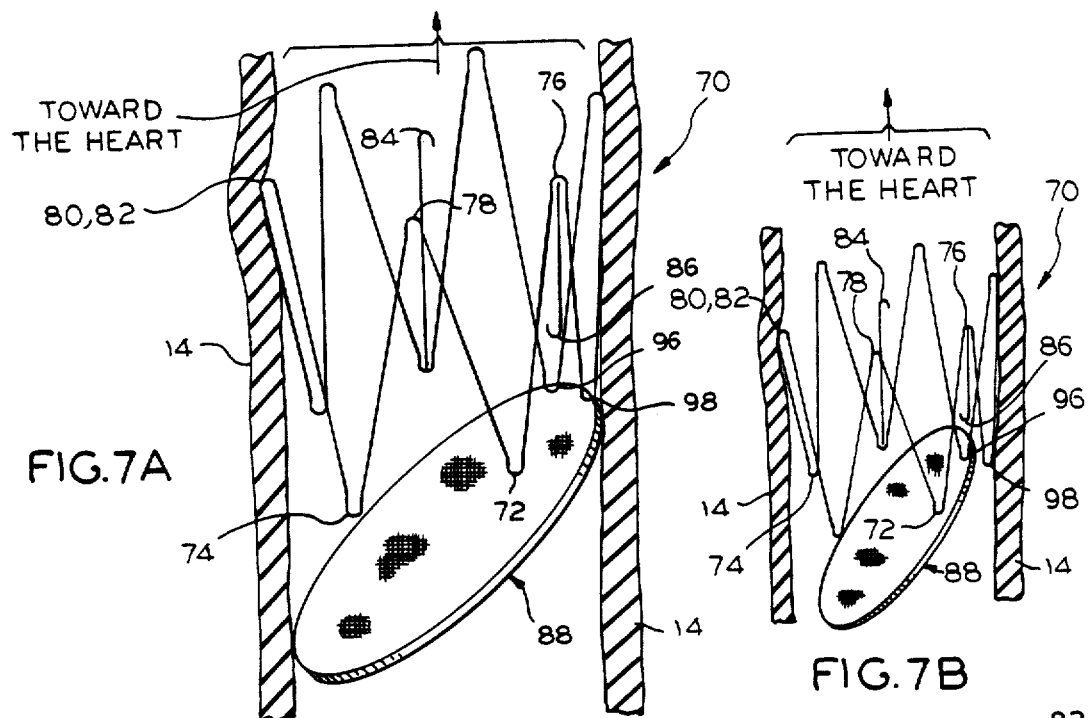
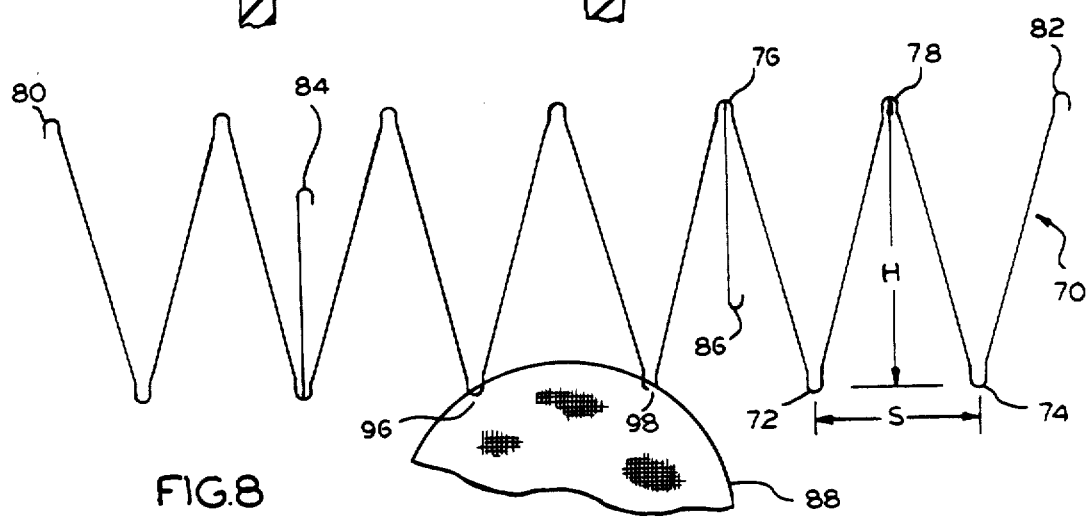
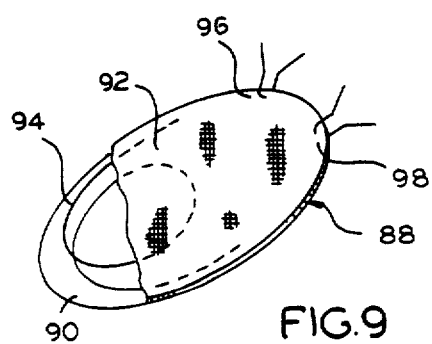

ARTIFICIAL HEART VALVE FOR IMPLANTATION IN A BLOOD VESSEL

This invention relates to heart valves and more particularly to artificial heart valves for installation in a blood vessel, such as the aorta, or the like, when the patient or the heart itself is in such a deteriorated condition that it is too risky to perform open heart surgery. These patients are sometimes described as New York Classification III and IV patients.

In general, artificial heart valves are implanted by a surgical procedure which opens the heart and installs the artificial valve in the location of the natural heart valve. This form of surgery has become common place. However, before it may be perforemed, the patient must be in a physical condition where he can survive the surgery and the heart must be sturdy enough to accept the valve.

Sometimes surgery is judged too risky to be performed because the prospects for survival are 50% or less. Nevertheless, it may still be possible to place an artificial "heart" valve in a blood vessel at some other location such as in the aorta, for example, in order to provide the normal heart valving function from that location. If necessary, a plurality of such artificial valves may be used at a number of different locations beyond a branching of the circulatory system after it leaves or before it enters the heart. Under some conditions, it might also be necessary to use a procedure called "Angioplasty" by which the natural heart valve may be placed in an inoperative, open position. Regardless of how much surgery is required, the invention enables it to be performed by the use of a catheter.

Accordingly, an object of the invention is to provide new and improved artificial heart valves which may be installed without having to resort to open heart surgery. In this connection, an object is to provide artificial heart valves which may be implanted in blood vessels instead of in the heart itself. Here, an object is to anchor the artificial heart valve so that it cannot migrate through the blood circulatory system.

Another object of the invention is to provide an artificial heart valve which may be installed by a catheter.

In keeping with an aspect of this invention, a first embodiment of the invention uses a clip having a form which is somewhat reminiscent of a safety pin. A disk is mounted thereon to open or close a passage through a vessel in the blood circulatory system, responsive to the ebb and flow of blood under the pumping action of the heart. The clip has a shape which prevents the disk from migrating through the circulatory system. The disk is a support made of stainless steel wire having a flap valve disk of ripstock nylon sewn thereto. A second embodiment has a STENT which anchors the flap valve.

A preferred embodiment of the invention is shown in the attached drawing, in which:

FIG. 1 schematically illustrates a human heart, a small fraction of the blood circulatory system associated therewith, and the inventive artificial heart valve in place in aorta;

FIG. 2 is a perspective view of a clip and disk which together form a first embodiment of the inventive heart valve;

FIG. 3 is a perspective view of the disk with a part broken away to show the construction thereof;

FIG. 4 shows a pair of telescoping catheters which are used to install the inventive heart valve;

FIG. 5 schematically shows the inventive valve in a closed position;

FIG. 6 schematically shows the valve in an opened position;

FIG. 7A, 7B are perspective views showing closed and open valve positions respectively of a second embodiment of the invention which uses a somewhat crown shaped STENT to support the artificial heart valve;

FIG. 8 is an alternative view showing the STENT laid out in a single plane; and

FIG. 9 is a perspective view which shows the construction of the flap valve that is used in the second embodiment.

A human heart 10, with some of the associated circulatory system, is shown in FIG. 1 with an artificial heart valve 12 in the aorta. The assumption is that the patient is too weak to have an acceptable chance of survival if open heart surgery is performed, to install the usual form of artificial replacement valve inside the heart itself. Nevertheless, it may be possible to install the inventive valve at another location which may be reached by a catheter. The artificial heart valve 12 is preferably installed in the aorta 14; however, it may be placed at some other suitable location in the circulatory system if the aorta cannot accept it. For example, it may be placed as at one of the locations 16, 18 or 20.

One embodiment of the inventive valve (FIG. 2) comprises a clip 22 having a shape somewhat reminiscent of a safety pin i.e. a single piece of wire is shaped to have two struts or lever arms 24, 26 with a coiled section 28 between them. Preferably, the wire is stainless steel, 0.016-inch in diameter. In one embodiment, the strut 24 is 13/16-inch long and the strut 26 is one-inch long. A barb or small bent foot area 30 (3/32-inch long) is formed on the free end of strut 26 in order to provide a barbed end. The foot or barb 30 was bent at an angle A which is slightly greater than 90°—approximately 100° in the exemplary embodiment. A second barb may be placed on strut 24; however, it has been found to be unnecessary and it makes the implantation more difficult. Two beads or drops of solder 32, 34 are attached to strut 26 to provide stops for holding a disk 36 in position, one bead being above and the other bead being below a location where disk valve 36 is located. The disk 36 is captured and loosely held between the two beads so that it may move up or down in the manner of a flap valve. The solder should be a material which is inert when in the human body.

It should be noted that the disk is located about midway along the strut 26. If it is placed closer to coil 28, the strut 24 might interfere with the valving action. If it is placed closer to the end 30, the flap valve disk 26 might invert within the blood vessel.

The construction of disk 36 is shown in FIG. 3. A support 40 is made of stainless steel wire about 0.014 inches in diameter and bent into a somewhat "W-shape". The object is to use about the smallest diameter wire possible considering the need for support. A pair of disks 42, 44 made from ripstock nylon are placed on opposite sides of the support 40 and then the entire perimeter of the nylon disks is sewn together and to the support 40 by a monofilament nylon line 46—a part of the stitching being shown at 47, 47. The outside arms 48, 50 of the "W-shape" are captured by the stitching 47, 47 along the periphery of the nylon disks, as the sewing is completed. The support 40 may be further tied to the nylon disks by 6.0 nylon stiches or sutures 51. It should be noted that the opposite ends of the flap are unsupported which allows some regurgitation of blood. The object in this limited amount of regurgitation is to avoid applying too much stress upon the walls of the blood vessel.

A suitable hole 52 is formed through the nylon disks 42, 44 at and within the bight 54 of the support's W-shape. This hole 52 may be formed in any suitable manner as by using the end 30 as a needle to simply pierce the nylon. However, if a hot needle, approximately the diameter of wire 26, is passed through the nylon, it will melt the nylon and, in effect, form a reinforcing grommet of molten plastic surrounding the hole 52.

The wire 26 fits through the hole 52. The two beads or drops of solder 32, 34 prevent the disk 36 from moving any significant distance along the wire 26 while providing enough play for the valve movement.

The installation of the invention valve is shown in FIGS. 4,5. The outer one 56 of a pair of telescoping catheters 56, 58 is passed through a vessel in the blood circulation system until end 60 is in the place which has been selected for the artificial heart valve implant position. For example the catheter may be placed in the femoral artery. Then, the inner catheter 58 is passed through the outer catheter 56 until emerges from the end 60. Thereafter, the clip 22 and valve disk 36 are pushed out of the inner catheter 58 and into the adjacent blood vessel. In one embodiment, the catheters were 14 to 16-french size (4-5.3 mm diameter).

As clip 22 emerges, its spring tension causes it to spread apart and to engage the adjacent walls of the surrounding artery or vein. For example, FIGS. 5, 6 show the clip 22 in place within aorta 14. Preferably the opposite tip ends of the wire forming the clip 22 may slightly penetrate the aorta wall without passing through it. The angles of the wire at the points of contact with the blood vessel help control the amount of penetration that occurs.

In this position, the disk 36 acts as a flap valve which is operated responsive to the ebb and flow of blood under the pressure created by the pumping heart. When the heart squeezes the blood out toward the circulatory system, the increase in blood pressure blows the flap valve disk 36 to an open position (FIG. 6), enabling blood to flow out. During the part of the cycle while the heart filling with blood, the heart is would tend to draw blood out of the aorta and back into the heart. However, this tendency creates a back pressure which presses the flap valve disk 36 into a closed position which seals the aorta 14. Therefore, the blood cannot return from the aorta to the heart.

The second embodiment is anchored by a modified STENT 70 (FIGS. 7, 8). It is thought that the original design of the STENT is attributed to Dr. Cesore Gianturco. A STENT is a cylindrical device or somewhat crown shaped (FIG. 7) which is made by bending wire into a zig-zag shape (FIG. 8). More particularly, in one embodiment, a stainless steel wire which is 0.018 inches in diameter is bent into a plurality of sections S, each of which has a height H. In the embodiment being described, section S was approximately 1 cm, as measured from peak 72 to peak 74 when the STENT is relaxed. Height H was about 2 cm. There were six peaks on each side of the STENT as shown as 72, 74, 76, 78, by way of example. Of course, these sizes and numbers of peaks are cited by way of example. Any suitable sizes and number of peaks may be used.

Once the STENT is bent into the described state, it has the appearance which is seen in FIG. 8. Then, it is wrapped to make a cylinder as shown in FIG. 7, and end 80 is joined to end 82 in any suitable manner, thereby providing an appearance which could, perhaps, be described as the appearance of a crown. Two oppositely disposed barbs or hooks 84, 86 are attached to the STENT in any suitable manner in order to snag the adjacent blood vessel wall regardless of the direction the STENT is likely to move. The barbs or hooks 84, 86 enter but do not pass through the vessel walls. The manner of attaching points 80, 82 and the barbs or hooks 84, 86 is irrelevant. However, the solder or other bonding agent should be inert when in the human body.

The flap valve 88 (FIG. 9) is formed by two disks of ripstock nylon 90, 92 which are bonded around the edges by any suitable bonding agent. The nylon layer 92 is here shown as broken away at 93 to reveal an internal support which is in the form of a wire 94 that is looped, as shown, and which is positioned between the nylon disks. Preferably, the wire 94 is free to slide around between the nylon disks 90, 92 in order to allow a small amount of regurgitation of blood to relieve pressure on the vessel wall.

The flap valve 88 is bonded in any suitable manner to the STENT at 96, 98. The wire forming the STENT may also be threaded through the fabric forming the flap valve. The barbs or hooks 84, 86 are located on opposite sides of the flap valve 88.

The embodiment of FIGS. 7-9 is installed and operates in substantially the same manner that the embodiment of FIGS. 1-6 is installed and operated. More specifically, FIG. 7A shows the valve 88 closed against the blood vessel wall 14, in a manner which is similar to the showing of FIG. 5. The open valve position (FIG. 7A) is similar to the position shown in FIG. 6.

An advantage of the invention is that it may be placed in different locations in the circulatory system. The embodiment of FIGS. 1-6 may be loaded into a catheter, as shown in FIG. 4, so that the end 28 emerges first. Or, it may be turned around so that the tips of the wire emerge first (end 28 last). The embodiment of FIGS. 7-9 may also be loaded to valve in either direction. Thus, depending upon the selected position where it is located, the valve may have either of two orientations depending upon the desired direction of the blood flow. In some cases, it may be possible that a patient's individual needs might require several valves on opposite sides of the heart.

Those who are skilled in the art will readily perceive how to modify the invention. Therefore, the appended claims are to be construed to cover all equivalent structures which fall within the true scope and spirit of the invention.

The claimed invention is:

1. An artificial heart valve comprising a wire bent into a shape which anchors said wire in a position within a blood vessel, said wire being sized and shaped for complete containment within said vessel and having at least one means for snagging the internal wall surface of said blood vessel without completely piercing it, and a flap valve attached to said wire, said flap valve being a disk which is free to open and substantially close approximately the entire surface space defined by the internal wall surface within the vessel responsive to the ebb and flow of blood caused by a pumping heart.

2. The heart valve of claim 1 wherein said bent wire is a single piece of wire which is in a form of two lever arms with a coiled selection between them.

3. The heart valve of claim 2 wherein said means for snagging is at least one barb associated with said bent wire for entering but not passing through the wall of said blood vessel.

4. An artificial heart valve compising a wire bent into a shape which anchors said wire in a position within a blood vessel, said bent wire being in the form of a wire bent into a zig-zag shape, the ends of the wire being joined to form a cylinder, said wire having at least one means for snagging the wall of said blood vessel without completely piercing it, and a flap valve attached to said wire, said flap valve being a disk which is free to open and close the internal space within the vessel responsive to the ebb and flow of blood caused by a pumping heart.

5. The heart valve of claim 4 wherein said means for snagging is at least one barb associated with said bent wire for entering but not passing through the wall of said blood vessel.

6. The heart valve of claim 4, wherein said flap valve comprises at least one plastic disk member which is loosely attached to said wire.

7. The heart valve of claim 3, wherein the flap valve is a pair of plastic fiber disks with a support member positioned between said plastic fiber disks.

8. An artificial heart valve comprising a wire clip formed by a single piece of wire that is shaped into two struts with a coiled section separating them, said two struts forming an acute angle with said coil at the apex of the angle, a disk valve threaded onto one of said struts, and means on said one strut for somewhat loosely holding said disk in a particular position on said one strut, said holding looseness being adequate to enable said disk to perform as a flap valve performs when said clip is positioned in a vessel of a blood circulation system.

9. The heart valve of claim 8 wherein said wire clip is a single piece of stainless steel wire which is about 0.016-inches in diameter.

10. The heart valve of claim 8 wherein said flap valve comprises two plastic disks with a support member between them, said support member being a single piece of wire bent into approximately a W-shape with the perimeter of said plastic disk being joined to the free arms of said W-shape, and a hole in said plastic at and within the bight of said W-shape, said one strut being threaded through said hole.

11. The heart valve of claim 10 wherein a hole having a melted perimeter extends through said pair of plastic disks at the location of and within the bight of said W, said plastic fusing and forming a unitary grommet surrounding said hole.

12. The heart valve of claim 10 wherein said two plastic fabric disks are sewn together at the peripheries thereof, and wherein said two plastic disks and said support means are held together with sutures.

13. The heart valve of claim 12 wherein said means for loosely holding said disk is a part of beads of solder on said one strut, one bead being on said one strut at a position above said disk and the other bead being on said one strut at a location below said disk.

14. The heart valve of claim 8 wherein said particular position is approximately the mid point on said one strut.

15. The heart valve of claim 5 wherein a tip end of said one strut is bent outwardly at an angle of approximately 100° to project toward the wall of said blood vessel.

16. The heart valve of one of the claims 2, or 8 wherein said flap valve is made of at least one disk of a plastic member which is loosely attached to said wire.

17. The heart valve of one of the claims 2, or 8 wherein the flap valve is a pair of plastic fiber disks with a support member positioned between said plastic fiber disks.

18. An artificial heart valve comprising a STENT formed by a wire which is bent with a zig-zag shape into the form of a cylinder which is somewhat reminiscent of a crown, at least one barb attached to said STENT for preventing a migration thereof within a blood vessel, and a flap valve attached to said STENT for opening and closing the blood vessel responsive to the ebb and flow of blood being pumped by a heart.

19. The heart valve of claim 18 wherein said flap valve is made of at least one disk of a plastic member which is loosely attached to said wire.

20. The heart valve of claim 18 wherein the flap valve is a pair of plastic fiber disks with a support member positioned between said plastic fiber disks.

21. A combination of an artificial heart valve and a catheter for locating said valve within a blood vessel, said valve comprising a bent wire having a configuration which prevents it from migrating within a blood vessel, a flap valve means associated with said bent wire with means for holding said flap valve in place on said wire, said flap valve being a reinforced plastic disk, and catheter means for inserting and movement to a selected location in a blood vessel where said heart valve is to be placed, said heart valve having a size and flexibility whereby it may be forced through and out the end of said catheter at said selected location, said bent wire having a spring tension which causes it to spread and attach itself to a wall of said blood vessel.

22. The combined heart valve and catheter of claim 21 wherein said heart valve has a size and flexibility such that it may be inserted through said catheter in either of two orientations whereby said flap valve may be selectively positioned to open in either of two directions within said blood vessel depending upon the desired direction of blood flow.

23. The combined heart valve and catheter of claim 18 wherein said catheter has outer and inner telescoping tubes, said outer tube moving to said selected location, the inner tube moving through said outer tube to deliver said heart valve.

24. The combined heart valve and catheter of claim 23 wherein said flap valve has a pair of plastic disks joined around the periphery thereof and a reinforcing bent wire support in the space defined by said joined periphery, said support leaving some unsupported periphery on said fiber disks to provide a controlled amount of blood regurgitation during closed valve conditions.

25. An artificial heart valve comprising a wire bent into a shape which anchors said wire in a position within a blood vessel, said wire having at least one means for snagging the wall of said blood vessel without completely piercing it, and a flap valve attached to said wire, said flap valve being made of at least one disk of a plastic member which is loosely attached to said wire, said disk being free to open and substantially close the internal space within the vessel responsive to the ebb and flow of blood caused by a pumping heart.

26. An artificial heart valve comprising a wire bent into a shape which anchors said wire in a position within a blood vessel, said wire having at least one means for snagging the wall of said blood vessel without completely piercing it, and a flap valve attached to said wire, the flap valve being a pair of plastic fiber disks with a support member positioned between said plastic fiber disks, said flap valve being free to open and close the internal space within the vessel responsive to the ebb and flow of blood caused by a pumping heart.

27. The heart valve of one of the claims 26, 21, or 20 wherein said flap valve is a pair of confronting disks made of a plastic fabric, the edges of which are joined around the periphery thereof, and said support member is a shaped piece of wire positioned between said disks and within the space defined by said joined edges.

* * * * *